United States Patent
Witteveen et al.

(10) Patent No.: US 8,057,784 B2
(45) Date of Patent: Nov. 15, 2011

(54) PARTICULATE FLAVORING COMPOSITION

(75) Inventors: Frans Witteveen, Leusden (NL); Fabio Campanile, Amsterdam (NL)

(73) Assignee: Quest International B.V., Naarden (NL)

( * ) Notice: Subject to any disclaimer, the term of this patent is extended or adjusted under 35 U.S.C. 154(b) by 861 days.

(21) Appl. No.: 10/591,570

(22) PCT Filed: Mar. 4, 2005

(86) PCT No.: PCT/NL2005/000160
§ 371 (c)(1),
(2), (4) Date: Apr. 26, 2007

(87) PCT Pub. No.: WO2005/084458
PCT Pub. Date: Sep. 15, 2005

(65) Prior Publication Data
US 2007/0274930 A1    Nov. 29, 2007

(30) Foreign Application Priority Data
Mar. 4, 2004 (EP) .................................... 04075741

(51) Int. Cl.
*A61K 8/00* (2006.01)
(52) U.S. Cl. .......................................... 424/49; 424/489
(58) Field of Classification Search ................ 424/49
See application file for complete search history.

(56) References Cited

U.S. PATENT DOCUMENTS

| | | | | |
|---|---|---|---|---|
| 2,886,446 A * | 5/1959 | Kramer et al. | ................ | 426/5 |
| 2,886,449 A | 5/1959 | Rosenthal et al. | | |
| 4,032,350 A * | 6/1977 | Greenstein | ................ | 106/1.13 |
| 6,190,722 B1 * | 2/2001 | Kim et al. | ................ | 426/650 |
| 2002/0159957 A1 | 10/2002 | Lages et al. | | |
| 2003/0082272 A1 | 5/2003 | Bouwmeesters et al. | | |
| 2004/0037890 A1 * | 2/2004 | Burger et al. | ................ | 424/499 |

FOREIGN PATENT DOCUMENTS

| | | |
|---|---|---|
| EP | 839516 A1 * | 5/1998 |
| EP | 1252828 | 10/2002 |
| WO | WO 9117821 | 11/1991 |
| WO | WO 9117821 A * | 11/1991 |
| WO | WO 0007463 | 2/2000 |

OTHER PUBLICATIONS

CAS Registry Record for Substance 139-44-6. Entered STN Nov. 16, 1984. 3 pages.*
CAS Registry Record for Substance 57-50-1. Entered STN Nov. 16, 1984. 2 pages.*

* cited by examiner

*Primary Examiner* — Frederick Krass
*Assistant Examiner* — Isaac Shomer
(74) *Attorney, Agent, or Firm* — Abelman, Frayne & Schwab

(57) ABSTRACT

The present invention relates to particulate compositions comprising controlled release particles wherein discrete elements of flavouring-containing fat are dispersed in a gelatine matrix, the particles containing; 0.1-40 wt %, preferably 5-30 wt % of flavouring; 10-70 wt %, preferably 20-50 wt % of gelatine; and 0.1-75 wt %, preferably 5 -0 wt % of fat, the fat having a melting point of at least 35° C.; the particles having a volume weighted average diameter of 50-1500 μm. The particulate composition according to the present invention will release the flavouring comprised therein under specific conditions e.g. under the influence of shear forces, heat and/or moisture. The release rate upon consumption can be affected by varying the relative amounts of gelatine and fat and the gelling strength of the gelatine. These compositions are therefore particularly suitable for imparting longer lasting taste sensation to confectionaries, in particular chewing gum, and to toothpaste.

17 Claims, 2 Drawing Sheets

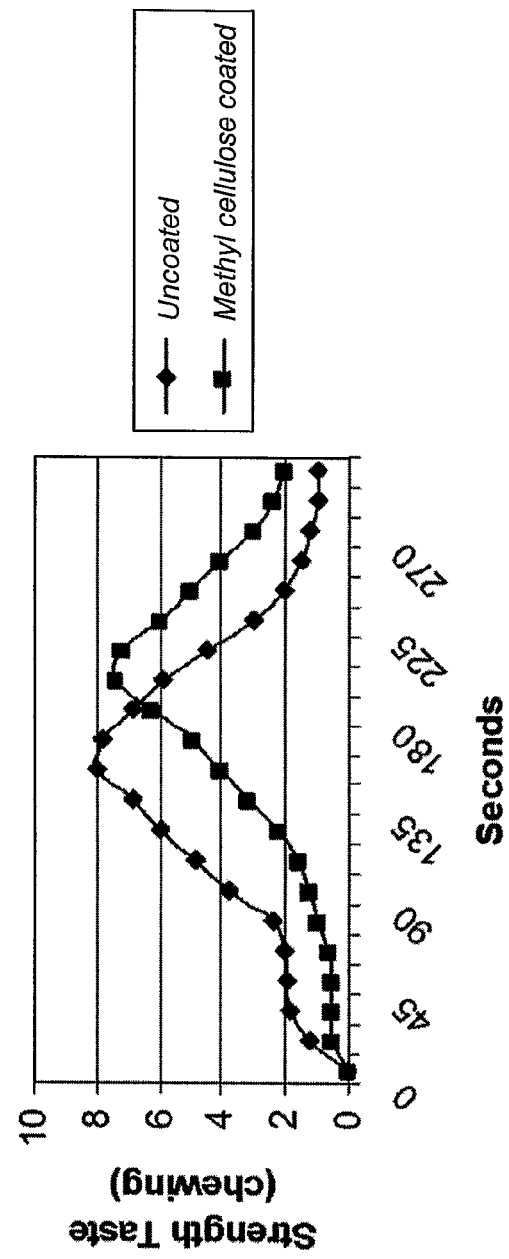

PARTICULATE FLAVORING COMPOSITION

FIELD OF THE INVENTION

The present invention relates to the field of flavouring of orally consumed compositions. More particularly it concerns encapsulation of volatile flavouring components thereby providing protection thereof against e.g. moisture and oxidation and allowing release of the flavouring in a controllable manner under specific conditions e.g. under the influence of shear forces, heat or moisture, as occur, for instance, during mastication. The encapsulates according to the invention are particularly suitable for flavouring confectionery products, such as chewing gums, or toothpastes.

BACKGROUND OF THE INVENTION

Encapsulation systems represent an important field of interest for the flavour industry. Encapsulated systems are designed to achieve two kinds of objectives.

The first goal relates to the function of protecting the ingredients entrapped in such systems. In fact, these systems must be capable of protecting an active material encapsulated therein from different kinds of retrogradation and at the same time of preventing the escape of the active material, especially of volatile flavouring component(s). Oxidation of flavours, such as essential oils, resulting in off-notes, poses serious problems for the food industry. Carbohydrates as a class offer a food-acceptable substrate in which volatiles and aromatics have been encapsulated with a certain degree of success. However most water-soluble carbohydrates are hygroscopic and will not reliably hold the encapsulate for long periods. The stabilisation of encapsulation systems therefore remains a critical issue in the field.

Another objective, that is always targeted for an encapsulated system, is to control (depending on the final application) the release of the active ingredient. In particular, if the active is volatile, it is generally of much importance to effectively prevent its release during storage, but at the same time to ensure that the encapsulation system will release the volatile active ingredient during use, triggered by conditions that are typical of such use.

A considerable amount of work has been performed relating to flavouring orally consumed compositions such as chewing gum, chewable medicinal tablets, chewing tobacco and toothpaste, whereby such orally consumed substances produce a flavour impact both initially and over an extended period of time. Problems have arisen in attempting to create encapsulates wherein part of the flavour is released immediately during e.g. mastication, whereas another part provides a sustained release of such flavour.

It is well known that the chewing gum base acts as a 'sink' for the added non-encapsulated flavour. In fact, the addition of non-encapsulated flavours to gum bases, as is still conventionally practised in the field, results in the release of only 20-40% of the total flavour during consumption, while the rest remains entrapped in the gum base. Moreover, chewing gums presently on the market have the following problems: (1) 1.0% or more of expensive flavour oil is required to obtain acceptable initial flavour perception (10 times that required in other confections) due to the fact that flavour oils have a great affinity for the chewing gum base, become locked in, and are thus not perceptible, as shown by analysis of cud after 4 hours of chewing wherein 80% of the added flavour still remains; and (2) even at 1.0% or more flavour oil levels, acceptable perception levels last only about 2-3 minutes.

Instead of simply adding flavour ingredients as such to gum bases, encapsulation in colloids such as gum arabic, maltodextrin or proteins has been proposed in the art as an alternative route to improve the efficient delivery of flavour.

U.S. Pat. No. 1,526,039, for example, teaches that if an essential oil or flavouring is combined with chewing gum base in a finely divided condition, and the particles of the flavouring or oil are encased in a suitable matrix so as to prevent contact with the gum base during manufacture, the deleterious effect of this contact on the flavour properties of the gum is thus prevented or largely reduced. By preparing an emulsion of the essential oil and an emulsifying material, which includes e.g. common gums and gelatine, the essential oil is divided into fine particles and these particles are encased in the emulsifying material, so that when the emulsion is added to the gum mass, the essential oil is prevented from coming into direct contact with the base. The physical form of these particles and the properties of the ingredients prevent the control of the flavour release and intensity.

U.S. Pat. No. 2,886,440 teaches a method of preparing a chewing gum characterised by "extended flavour perception time" and high degree of flavour release by incorporating therein a spray-dried composition comprising a volatile, water-immiscible flavouring agent encapsulated within finely divided particles of gelatine, and substantially uniformly distributing said gelatine encapsulated flavouring agent within an all-enveloping mass of a chewable gum base. The use of separate "fixed" and "unfixed" flavour portions is also taught.

U.S. Pat. No. 2,886,446 teaches a chewing gum comprising (i) smaller particles of gelatine characterised by fast release of flavour and (ii) larger particles of gelatine characterised by slower release of flavour, each of the gelatine particles containing dispersed therein, in dried emulsion form, discrete micro-droplets of a volatile water-immiscible flavouring agent, and an all-enveloping mass of a chewable gum base within which the particles are substantially uniformly distributed whereby the flavour is released substantially evenly and uniformly over the extended chewing time. This document further discloses that the grade, type or bloom strength may vary widely. When a rapid release is desired it is preferred to use a gelatine having a Bloom less than 50. When slower release is desired the Bloom preferably will be above 200, according to U.S. Pat. No. 2,886,446.

In U.S. Pat. No. 4,386,106 controlled, delayed release encapsulated flavour particles are disclosed comprising a base powder of partially hydrophilic and slowly soluble material, e.g. a combination of gelatine with gum arabic and a plasticizer such as glycerol, which entraps the flavour and a coating material that is insoluble in but has affinity for the chewing gum base. The essential features of these encapsulates are: (I) the core matrix which entraps and prevents loss of the volatile flavour component during drying and yet which is partially hydrophilic to give quick and sustained release of flavour; and (II) the water insoluble coating which delays flavour release and prevents the flavour from dissolving, and thereby being indefinitely entrapped, in a chewing gum base. The time of flavour release can be controlled by varying parameters such as particle size, the choice of flavour, the bloom strength of the gelatine used in the base matrix, as well as the use of other components in the matrix, such as maltodextrin and/or gum arabic, the amount of water insoluble coating and by treating the outer surface of the base powder matrix to seal and insolubilize the outer surface thereof, e.g. by the use of cross-linking agents.

U.S. Pat. No. 5,116,627 discloses chewing gum compositions comprising a chewing gum base having dispersed therein sweetener-bearing polymeric particles and/or flavourbearing polymeric particles, which polymeric particles comprise a water-soluble polymer and a water-insoluble polymer being physically associated with each other and in such a manner that one is in the form of discrete entities in a matrix of the other. The active ingredient, e.g. a flavour oil, is incorporated in either or both of the water-soluble and the water-insoluble polymer. The particle size and relative ratio of water-soluble to water-insoluble polymer can be varied to release a lesser proportion of the flavour and/or sweetener composition during mastication initially and a greater quantity on continuous mastication of the chewing gum.

In WO 91/17821 microcapsules containing a flavour component embedded in a matrix material comprising a colloid, such as a gum, modified starch, gelatine, or a dextrine; and optionally saccharides and waxes are disclosed. The wax can be added in order to extend the release of flavour from the matrix, and is preferably a relatively hard, water-insoluble wax. These microcapsules are suitable for use in confectionery products such as chewing gum.

US 2003/082272 discloses a method of preparing water insoluble gel beads consisting of a porous alginate matrix containing entrapped flavour solvent, such as fat or vegetable oil. The beads are loaded with flavour by mixing a liquid flavour with the particles. Since alginate gels have relatively large pores, other macromolecules may be added as a filler material. Suitable filler materials according to US 2003/082272 include dextrins, gums, cellulose derivatives and proteins such as gelatine. Beads having a matrix comprised of approximately 6.5 wt % of gelatine, 6.5 wt % of alginate and 82.5% of miglyol are disclosed in this document.

In spite of all prior-art attempts to provide satisfying controlled-release flavouring compositions as mentioned above there is thus still a need for improved flavouring compositions for use in orally consumed compositions, particularly in chewing gum, which are capable of further extending the satisfactory chewing time thereof, and/or which require the use of less flavouring.

SUMMARY OF THE INVENTION

Surprisingly, it has now been found that an encapsulation composition comprising gelatine and a high melting fat, in addition to providing sufficient protection against e.g. oxygen and moisture, during storage and processing, exhibits excellent controllable delayed release-characteristics of substantially all of the initially encapsulated flavourings during consumption.

More particularly, it was found that these advantageous properties are provided by a particulate flavouring composition comprising particles that contain 0.1-40 wt % of flavouring, 10-70 wt % of gelatine and 0.1-75 wt % of fat having a melting point of at least 35° C. and that is further characterised by a volume weighted mean particle diameter in the range of 50-1500 µm. In addition, the aforementioned particles are characterised in that they comprise flavouring-containing discrete elements of fat dispersed in a gelatine matrix.

In particular, it was found that the time of occurrence of the flavour release peak, i.e. the rate of release from such encapsulates upon e.g. mastication, can be controlled very effectively by adjusting the relative amounts of fat and gelatine in the matrix, by varying the bloom strength of the gelatine and by manipulating the size of the particles.

Without wishing to be bound to theory, it is believed that the particles according to this invention comprise a gelatine matrix with discrete elements of flavouring-containing fat dispersed therein. Upon consumption, the time of occurrence of the flavour release peak or flavour release rate is believed to be affected by the size and/or quantity of the water-insoluble fat elements and the gelling strength of the gelatine matrix. Accordingly particles comprising larger fat elements and/or high bloom value gelatine, will display a more delayed release of the flavouring upon consumption compared to particles comprising smaller fat elements and/or low bloom value gelatine.

In EP 1 252 828 powdered flavours coated with a coating agent comprising a lipid which is solid at ordinary temperature, e.g. hydrogenated vegetable oil, and at least one of an edible water soluble additive and/or an edible polymer substance, e.g. gelatine, are disclosed. The flavouring may be powdered by dissolving and mixing the aimed material in an aqueous solution of e.g. dextrin, natural gum, a protein such as gelatine or casein, and then (spray)drying. Hence, the particles according to this document comprise a flavouring encapsulated in a hydrophilic carbohydrate or protein matrix which is subsequently coated with a lipophilic coating material. In contrast, according to the present invention the flavouring is entrapped within discrete fat elements which are dispersed in the gelatine matrix.

The present invention also encompasses a flavour delivery system that contains a combination of two or more particulate compositions according to the invention, including a particulate composition providing a relatively fast flavour release and another particulate composition that provides a significantly slower flavour release.

Other aspects of the invention relate to the use of the present particulate composition and/or flavour delivery system for imparting controlled release characteristics to chewing gum and to a chewing gum containing such a composition or system.

Yet another aspect of the invention relates to the use of the present particulate composition and/or flavour delivery system in toothpaste, and to toothpaste containing said composition or system.

BRIEF DESCRIPTION OF THE DRAWINGS

FIG. 2 is a Time Intensity Graph which plots Strength of Time (chewing) vs. Time.

DETAILED DESCRIPTION OF THE INVENTION

Figure 1:
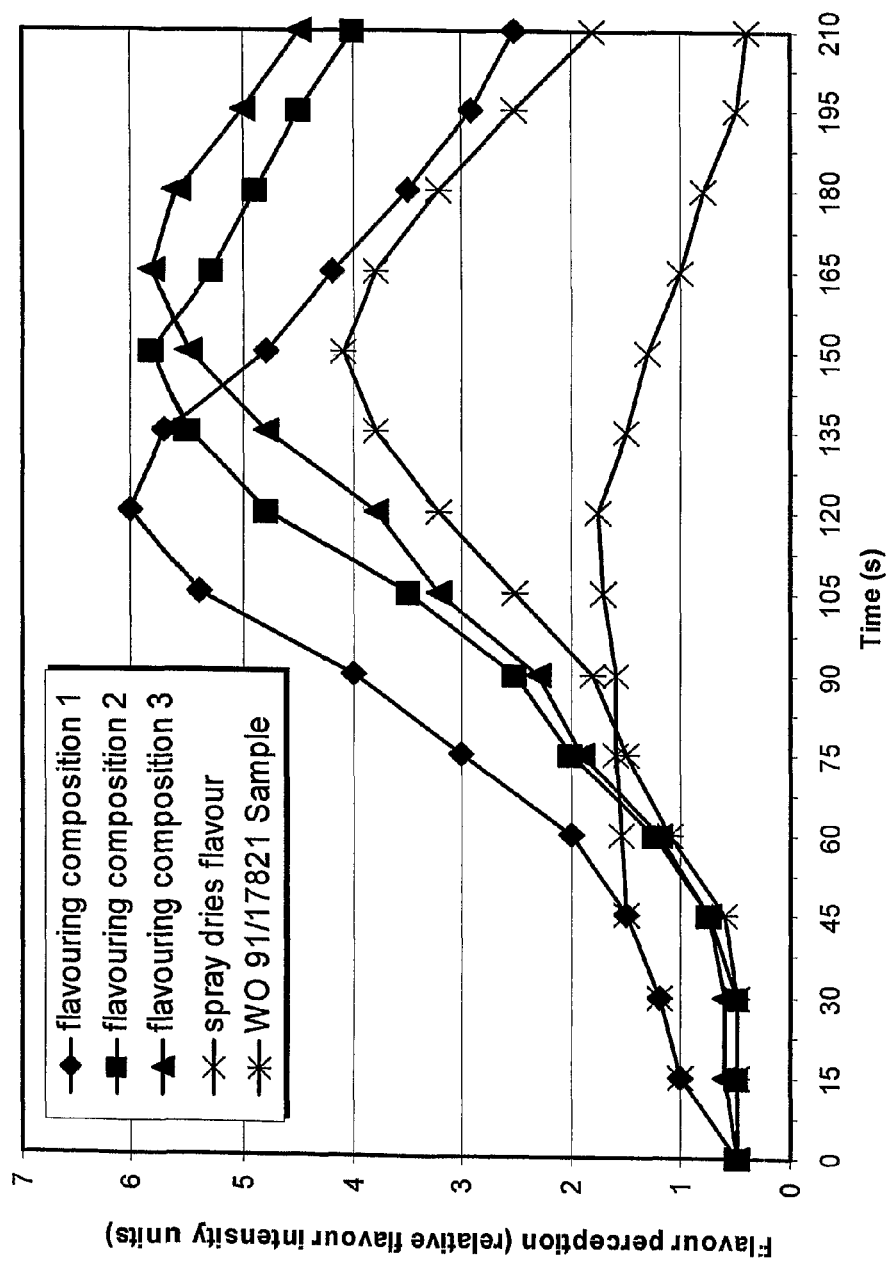
FIG. 1 is a graphical representation of flavour perception (relative flavour intensity units) which is plotted against Time.

Accordingly, the present invention in a first aspect relates to a particulate composition comprising controlled release particles wherein discrete elements of flavouring-containing fat are dispersed in a gelatine matrix, said particles containing:

0.1-40 wt %, preferably 5-30 wt % of flavouring;
10-70 wt %, preferably 20-50 wt % of gelatine; and
0.1-75 wt %, preferably 5-50 wt % of fat having a melting point of at least 35° C., said particles having a volume weighted average diameter of 50-1500 µm.

Throughout this document the terms "flavouring" and "flavour" are used interchangeably as they are deemed to be synonyms.

The term "flavour release peak" as used in this document refers to the moment during consumption when the flavour release rate reaches its maximum. Whenever reference is made in this document to the rate at which flavour is released this refers to the steepness of the flavour release curve. The flavour release rate is strongly correlated with the occurrence of the flavour release peak, i.e. a fast release rate usually is accompanied by an early occurrence of said peak and slow release rate with a late occurrence of the peak.

The term "volume weighted average diameter" refers to the volume based average diameter of the particles, which can suitably be determined using a Beckman Coulter LS Particle Size Analyzer or by employing a conventional sieving method.

The particles according to the present invention effectively entrap the flavourings and/or prevent degradation thereof during storage and processing, for example when incorporated in chewing gum, and will release the flavouring with a controllable delay upon mastication, the delay-time being dependent on the relative amounts of fat and gelatine, the Bloom number of the gelatine and the size of the particles.

Flavourings used in the present invention typically may include a variety of both natural and synthetic materials. They include single substances as well as complex mixtures of synthetic and/or natural substances. Flavourings are well-known in the art and are mentioned, e.g., in S. Arctander, Perfume and Flavor Materials of Natural Origin (Elisabeth, N.J., USA, 1996), in T. E. Furia et al, CRC Fenaroli's Handbook of Flavor Ingredients, 2nd Ed. (Cleveland, CRC Press Inc., 1975), and in H. B. Heath, Source Book of Flavors (The Avi Publishing Company Inc., Westport, Conn., 1981).

The encapsulation composition according to the invention, comprising gelatine and as defined herein before, may be used advantageously to encapsulate volatile or labile flavouring components which may be in liquid or in solid form, and which are typically insoluble in water. The flavouring present within the particulate composition of the present invention may contain as flavouring substances e.g. aldehydes, acetales, ketones, terpenes, esters, pyrazines and lactones. The flavouring may suitably contain essential oils, such as citrus or essential oils of herbs and spices that contain the aforementioned flavouring substances.

Examples of flavour ingredients which may be used within the scope of the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert.butylcyclohexyl acetate, isononyl acetate, vetiveryl acetate, vetiverol, α-hexyl-cinnamaldehyde, 2-methyl-3-(p-tert.butylphenyl)-propanal, 2-methyl-3-(p-isopropyl phenyl)-propanal, 3-(p-tert.butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentyl-cyclopentane, 2-n-heptyl-cyclopentanone, 3-methyl-2-pentyl-2-cyclopentanone, n-decanal, n-dodecanal, dec-9-en-1-ol, phenoxyethyl isobyutyrate, phenylacetaldehyde dimethylacetal, phenyl-acetaldehyde diethylacetal, geranyl nitrile, citronellyl nitrile, cedryl acetate, 3-iso-camphyl cyclohexanol, cedrylmethyl ether, isolongifolanone, aubepine nitrile, aubepine, heliotropine, coumarin, eugenol, vanillin, diphenyl oxide, hydroxy citronellal, ionones, methyl ionones, isomethyl ionones, irones, cis-3-hexenol and esters thereof and mixtures thereof.

The particulate composition according to the invention is particularly suited for providing a controlled release of menthol, mint and/or eucalyptus flavour in chewing gum applications. Thus, according to a very preferred embodiment of the present invention relates to particulate flavouring compositions wherein the flavouring is selected from the group of menthol flavouring, mint flavouring, eucalyptus flavouring and mixtures thereof.

In accordance with the present invention, gelatine of any type and grade may suitably be used, including for example gelatine derived from bone or skin, preferably from bone. Modified gelatines including e.g. gelatine metaphosphates, hardened gelatine (e.g. those treated with a cross-linking agent such as formaldehyde), heat-treated gelatines and others may also be employed. The Bloom strength of the gelatine that is used may vary widely and may suitably range from 0-300, especially 10-300. The degree to which the release of the flavouring composition from the matrix is delayed is partly determined by the Bloom or gelling strength of the gelatine. When a relatively fast release of the flavouring from the matrix upon consumption is desired, it is preferred to use a gelatine having a Bloom less than 150, more preferably less than 100. When a slow release of the flavouring upon consumption is desired the Bloom will preferably be at least 150, more preferably at least 200, most preferably at least 240. Gelatines having relatively high Bloom strength have a tendency to give hard, "crunchy" textures which may not be desirable in the manufacture and consumption of chewing gums. In cases where the texture of the end product is not particularly critical even higher Bloom strengths than the ones disclosed here may suitably be used. It may be clear to the skilled person that by using hardened gelatine the occurrence of the flavour release peak may be delayed as well, compared to non-hardened gelatine.

It is an essential element of the present invention that the particulate flavouring composition further comprises a high melting fat. The term "fat" as used throughout this document encompasses triglycerides, sucrose polyesters of fatty acids and combinations thereof. High melting fat in accordance with the present invention may be obtained by hydrogenation of vegetable oils and/or animal fats, or by isolating high melting fractions from these oils and fats. It was found that the moment at which the flavouring is released from the present particulate composition, particularly during e.g. mastication, can be delayed further by employing a fat that is substantially solid at mouth temperature. Consequently, in a particularly preferred embodiment, the fat contained in the present particles has a melting point of at least 35° C., more preferably of at least 38° C., most preferably of at least 45° C.

It is believed that when a flavouring component is encapsulated in a matrix comprising gelatine and fat according to the present invention a particulate composition is obtained wherein the flavouring and the fat are entrapped as discrete elements within a matrix containing the gelatine. Typically at least 90%, more preferably at least 95% of the flavouring is dissolved or dispersed homogeneously in the discrete fat elements. It is further believed that the relative quantities of the fat and gelatine can be varied to obtain the desired release characteristics; the quantity and/or relative size of the discrete fat elements will affect the time of occurrence of the flavour release peak and the rate of flavour release upon consumption. Typically, the mass weighted mean diameter of the discrete flavouring-containing fat elements will be in the range of 0.5-10 µm, preferably in the range of 0.8-3 µm.

The particulate composition according to the present invention will release the flavouring comprised therein under specific conditions e.g. under the influence of shear forces, heat and/or moisture, as occur during the consumption of the products they are incorporated in. These conditions are typically exerted during chewing, e.g. of confectioneries such as chewing gum, and brushing, e.g. of toothpaste. The term "consumption" as used herein therefore is meant to encompass chewing and brushing of the composition.

The amount of fat that is comprised in the particles may vary between 0.1 and 75 wt %, depending on the 'release-characteristics' that are desired. In order to provide a relatively slow release, the amount of fat contained in the particles preferably is at least 5 wt %. In case an even slower release is desired, e.g. in chewing gum applications, the amount of fat preferably exceeds 8 wt %, even more preferably it exceeds 10 wt %. It is furthermore preferred that the amount of fat does not exceed 65 wt %, more preferably it does not exceed 50 wt %.

The gelatine is comprised in the flavour and fat containing particles according to the invention in an amount of 10-70 wt %. The delay in the occurrence of the flavour release peak, e.g. during mastication, is, amongst others, dependent on the relative amounts of gelatine and fat comprised in the matrix. Typically, the present particles contain 20-50 wt % of gelatine in combination with at least 5 wt % fat.

The particles according to the present invention typically comprise 0.1-40 wt % of flavouring. Since the present composition is particularly effective in providing a sustained release of the flavouring contained therein, it is feasible to incorporate a substantial amount of flavouring in the present particles without causing an undesired initial "flavour burst". Consequently, in a preferred embodiment, the present particles contain at least 0.5 wt %, more preferably at least 2 wt % and most preferably at least 5 wt % of flavouring.

Particularly favourable release characteristics are observed if in the present particles the combination of flavouring and fat represents more than 35%, preferably more than 40% and more preferably at least 50% by weight of the combined amounts of flavouring, fat and gelatine contained in said particles.

As mentioned herein before, also the size of the particles of the particulate composition significantly affects the release-characteristics. It has been found that if the particles in the particulate composition have a volume weighted average diameter of at least 50 µm, they provide sufficient stability as well as a sufficiently sustained release. Preferably, said average diameter is at least 80 µm, more preferably at least 125 µm. Typically, the aforementioned average diameter will not exceed 1500 µm. In order to enable homogeneous distribution of flavouring throughout an endues product, it is preferred to employ articles having a volume weighted average diameter of not more than 1000 µm, more preferably of not more than 850 µm. It is furthermore preferred that at least 75 wt %, more preferably at least 90 wt %, of the particles has a diameter within the range of 80-1000 µm, more preferably within the range of 125-850 µm.

According to a preferred embodiment of the present invention the particulate flavouring composition further comprises a film forming carbohydrate. The film forming carbohydrate is suitably selected from the group consisting of gums, modified starches, cellulose derivatives and mixtures thereof Preferably, the film forming carbohydrate is selected from gums, modified starches and mixtures thereof. Particularly preferred but non-limiting examples of film forming carbohydrates are selected from the group of gums, such as gum arabic or gum acacia, modified starches, cellulose derivatives, such as methylcellulose, ethylcellulose, hydroxyethylcellulose, hydroxypropylcellulose, hydroxypropyl methylcellulose, carboxymethylcellulose and mixtures thereof. The film forming carbohydrate may be comprised in the particles in an amount of 0.1-10 wt %, preferably 2-6 wt %.

The particulate flavouring composition according to the present invention may further comprise a carbohydrate plugging material. With the term 'plugging material', as used herein, a material is meant that is used to modify in particular the glass transition temperature and the melting behaviour of the particle matrix, thereby providing an improved oxygen barrier to the encapsulated flavour and preventing flavour from leaking out of the encapsulate. The plugging material may suitably be selected from the group of mono, di and tri-saccharides, such as for example glucose, fructose, maltose, sucrose, raffinose, xylitol, sorbitol and mixtures thereof. These saccharides may also be provided in the form of materials having a high content of such sugars, such as fruit juice solids. Preferably, the plugging material is selected from maltose, sucrose, xylitol, sorbitol and combinations thereof. Even more preferably, in the instance where the flavouring composition is intended to be used in so-called 'sugar-free chewing-gum', the plugging material is selected from xylitol, sorbitol and combinations thereof. Plugging material is typically comprised in the particles of the present particulate composition in an amount ranging from 1-30 wt %, preferably 10-20 wt %.

The combination of flavouring, gelatine and fat in the present particulate composition typically represents at least 50 wt % of said composition. Preferably, said combination together with the optional ingredients film forming carbohydrate and carbohydrate plugger represent at least 70 wt %, more preferably at least 80 wt % and most preferably at least 90 wt % of the present particulate composition.

The bulk density of the present particulate composition is typically within the range of 300-700 g/l. Preferably the bulk density of the present composition is within the range of 400-600 g/l. Although particulate compositions such as those according to the present invention are generally obtained by drying emulsions of the particle components, such as disclosed in more detail hereafter, these compositions usually contain some water. Typically, the composition according to the present invention comprises 0-6 wt % of water, especially 0.3-4 wt % of water.

The controlled release particles present in the particulate composition may optionally comprise additional food-grade additives known in the art. Typical examples comprise artificial sweeteners, preservatives, colourants, fillers, etc. Typically, the combination of flavouring, gelatine and fat constitutes 50-100 wt %, preferably 70-100 wt % of the controlled release particles.

Besides the controlled release particles containing flavouring, gelatine and fat in the indicated amounts, the present particulate composition may contain other particulate material, such as sugar, colouring etc. Preferably, the particulate composition comprises at least 50 wt % of the controlled release particles. Even more preferably the composition contains at least 80 wt % of the controlled release particles. Most preferably the composition essentially consists of the controlled release particles.

The particulate compositions according to the present invention are typically obtained by drying emulsions comprising gelatine, fat, flavouring, and optionally a film forming carbohydrate, a plugger substance or any other desired additive, by any conventional process known in the art, such as spray-drying, drum drying, extrusion, fluidised bed processing or freeze drying. Preferably the emulsion is dried by fluidized bed processing or freeze drying. The freeze drying process is typically carried out by solidifying said emulsion in a workable shape, e.g. into 1 cm beads using a palletizing unit. The beads are then collected and subjected to a standard freeze drying process.

The emulsion for use in the drying process as mentioned above is preferably obtained by preparing an aqueous solution of the water-soluble components, which include the gelatine and optionally the plugger material and the film forming carbohydrate; and then adding thereto a mixture of the flavouring and the fat, which mixture may suitably have been prepared by dispersing the flavouring into the molten fat. The emulsion is suitably homogenised while being kept at a temperature above the melting point of the fat. The size of the fat droplets is closely monitored during homogenisation since, as mentioned before, the size and quantity of the discrete fat elements in the end-product particle affect the release characteristics of the flavour upon consumption. When the fat droplets in the emulsion have the desired size, the emulsion is subjected to a drying step.

The release-characteristics of the present particulate composition are advantageously manipulated by choosing a suitable combination of gelatine bloom strength, and relative amounts of fat and gelatine.

The relation between the bloom number, the relative amounts of gelatine and fat and a "relative flavour release rate value" of the particles upon consumption, expressed as x, can be defined by the formula:

$$((\text{Bloom number}/150)+(\text{wt \% gelatine}/30))*(\text{wt \% fat}/10)=x$$

In the instance where mixtures of gelatines with different bloom numbers are used, the mass weighed average bloom number of the mixture is conveniently used to estimate x.

In one particular embodiment a particulate flavouring composition is provided wherein the controlled release particles contain 10-70 wt % of gelatine, having a Bloom number of 0-300, 0.1-75 wt % of fat and 0.1-40 wt % of flavouring, wherein x is at least 0.8, which is characterised by a very slow release of the flavour. In a particularly preferred embodiment slow-release particulate compositions are provided wherein x is at least 0.8, more preferably at least 1.0, most preferably at least 2.0. Typically, x will not exceed 20, preferably it does not exceed 18. Particulate compositions comprising 10-70 wt % of gelatine, having a Bloom number of 0-300, 0.1-75 wt % of fat and 0.1-40 wt % of flavouring, wherein x is lower than 0.5, will release the flavouring relatively quickly upon consumption. These quick-release particulate compositions can be used to provide an early flavour burst and provide an advantageous alternative to unencapsulated flavours.

The controlled release particles of the present invention may advantageously be further coated with e.g. long chain hydrocolloid, such as but not limited to those selected from the group of polysaccharides, zein, shellac, cellulose derivatives and mixtures thereof. Particularly advantageous results can be obtained if the coating layer represents from 0.5-5 wt. % of the coated particles. Higher amounts of coating will result in an undesirable suppression of flavour intensity.

Surprisingly advantageous results are obtained when the present particles are coated with a cellulose derivative selected from the group consisting of methylcellulose, ethylcellulose, hydroxyethylcellulose, hydroxypropylcellulose, hydroxypropyl methylcellulose, carboxymethylcellulose and mixtures thereof. Said coating may be applied to the particles using any of the conventional coating techniques known in the art.

It was unexpectedly found that the application of an additional exterior coating with cellulose derivative effectively delays the flavour release without affecting the perceived flavour intensity. This is very surprising as usually delayed flavour release is accompanied by a reduction of perceived flavour intensity. This is because as a result of the retardation of the flavour release, the flavour release peak is effectively 'spread out' over a longer time period, meaning that the maximum release rate and hence the maximum flavour intensity is also diminished. Consequently, the methyl cellulose coated product of the present invention offers the advantage that it combines delayed flavour release with a sudden flavour intensity burst.

Another aspect of the present invention relates to a flavour delivery system comprising two compositionally different particulate flavouring compositions as defined above. More particularly, this aspect of the invention, is concerned with a flavour delivery system that comprises (a) 5-70 wt % of a first particulate composition as defined herein before wherein x is at least 1, and (b) 5-70 wt % of a second particulate composition as defined herein before wherein x is less than 1. According to another equally preferred embodiment a flavour delivery system is provided comprising (a) 5-70 wt % of a first particulate composition as defined herein before wherein x is at least 1, and (b) 5-70 wt % of a second particulate composition as defined herein before wherein the value of x is at least 20% lower than that of the first composition. In another preferred embodiment a flavour delivery system is provided that comprises (a) 5-70 wt % of a particulate composition as defined herein before wherein x is at least 1, and (b) 5-70 wt % of non-encapsulated flavour (liquid flavour) or any other immediate-release particulate flavouring composition known in the art. Due to the occurrence of several subsequent flavour release peaks during consumption of a product containing such flavour delivery systems, it is possible to design systems providing a long(er) lasting constant taste perception by the consumer upon consumption.

The present invention further relates to the use of the present particulate flavouring compositions and/or the flavour delivery systems for flavouring chewing gums. The chewing gum can be any type of chewing gum known in the art, the composition of which will be apparent to and/or available for the skilled person. Optionally the chewing gum is further coated with an often crunchy water soluble coating layer. In one preferred embodiment, the invention product is used to extend the satisfactory chewing time of the chewing gum by incorporating in the gum base one or more fractions of the controlled release particles, and optionally the liquid flavour. In an advantageous embodiment of the present invention the fast release fractions of the flavour delivery system, e.g. the liquid flavour or quick release particles that are used for providing an initial 'flavour burst', are incorporated in the outer coating layer of the chewing gum as well as in the gum base itself, and the present particulate composition is only incorporated in the chewing gum. In an even more preferred embodiment, the fast release fraction is incorporated in the coating and the slow release particulate composition in the chewing gum Chewing gums prepared with the present particulate controlled release compositions or systems will reach higher flavour levels and/or maintain highly perceptible flavour over an extended period of time, compared with the chewing gums presently known in the art.

In a particularly preferred embodiment a flavour delivery system as defined herein before is incorporated into chewing gum. Thus, a chewing gum can be provided that will deliver an essentially constant flavour sensation for several minutes. Also, this embodiment makes it possible to let a consumer experience subsequent distinct tastes, e.g. a lemon flavour during the first minute, followed by a mint flavour.

In yet another embodiment the present invention relates to chewing gum comprising the particulate flavouring composition or the flavour delivery system according to the present invention in an amount of 0.01-6 wt %, based on the total weight of the chewing gum composition, preferably 0.05-3 wt %. As described above the most preferred embodiments relate to chewing gums providing exceptionally long taste-perception and to chewing gums providing the experience of distinct subsequent flavours.

In another preferred embodiment the flavour delivery system or the particulate flavouring composition according to the present inventions is incorporated into toothpaste for imparting thereto the advantageous flavouring characteristics as described here-above.

Yet another embodiment of the present invention therefore relates to toothpaste comprising the particulate flavouring composition or the flavour delivery system according to the present invention in an amount of 0.01-6 wt %, based on the total weight of the toothpaste composition, preferably 0.05-3 wt %. The toothpaste can be any type of toothpaste known in the art, the composition of which will be apparent to and/or available for the skilled person.

EXAMPLES

Example 1

Different particulate flavouring compositions were prepared according to the present invention. The amounts of the different components that were used to prepare the emulsions are shown in table 1.

TABLE 1 emulsions for preparing particulate flavouring compositions

|  | Preparation | | |
| --- | --- | --- | --- |
|  | 1 | 2 | 3 |
| gelatine 240 (g) | 300 | 300 | 300 |
| Xylitol (g) | 110 | 110 | 110 |
| gum Arabic (g) | 29 | 29 | 29 |
| Water (g) | 880 | 880 | 880 |
| Menthol (g) | 120 | 150 | 260 |
| PO58 (g) | 32 | 150 | 600 |

Solutions are prepared by dispersing the first three components in water and mixing at 60° C. for 30 minutes. The menthol was dissolved in fully hydrogenated palm oil (type Admul P058 5Z03910 produced by Quest International B.V.) at 60° C. which is subsequently added to the aqueous dispersion and an emulsion is produced by homogenisation for 15 minutes at a temperature of 60° C. using an Ultra Turrax. This emulsion is then processed into round 1 cm frozen particles in a cryogenic pelletizer/breaker using liquid nitrogen. These deep frozen particles are subsequently loaded onto a batch freeze dryer, operating at a temperature of −45° C., with a vacuum of 1 mbar, a plate temperature of 20° C., during 48 hours of processing time. The resulting material is then grinded down to a particle size range of 125-1000 micron with D50~500 micron. This resulted in the particulate flavouring compositions shown in table 2

TABLE 2 particulate flavouring compositions prepared according to the present invention.

|  | flavouring composition | | |
| --- | --- | --- | --- |
|  | 1 | 2 | 3 |
| gelatine 240 (wt %) | 50 | 40 | 22 |
| Xylitol (wt %) | 18 | 14 | 8 |
| Gum Arabic (wt %) | 5 | 4 | 2 |

TABLE 2-continued particulate flavouring compositions prepared according to the present invention.

|  | flavouring composition | | |
| --- | --- | --- | --- |
|  | 1 | 2 | 3 |
| Water (wt %) | 2 | 2 | 2 |
| Menthol (wt %) | 20 | 20 | 20 |
| PO58 (wt %) | 5 | 20 | 46 |

Experiment 2

Each of the flavouring compositions according to example 1 was added to a chewing gum bases having the following composition:

| Gumbase | 712 g |
| --- | --- |
| Sorbitol | 279 g |
| Glycerine | 8.2 g |
| Aspartame | 0.8 g |
| Flavour particles | 15 g |

Additionally similar chewing gums were prepared using conventional spray dried flavour particles, and controlled release particles of WO 91/17821, prepared according to example 4 thereof. The composition of these particulate compositions is shown in table 3.

TABLE 3 particulate flavouring compositions prepared according to the method of WO 91/17821

| Spray dried flavouring composition | controlled release particles of WO 91/17821 |
| --- | --- |
| 2 wt % water | 1 wt % water |
| 38 wt % Capsul | 73 wt % gelatine 240 |
| 40 wt % Malto Dextrine MD20 | 6 wt % carnauba wax |
| 20 wt % Menthol 20 | 20 wt % menthol |

In all instances the same amount of flavouring particles was incorporated into the chewing gum. The five different chewing gums were tested for the release of the menthol flavour upon chewing by a sensorial panel. The perception of taste was expressed in relative intensity units by the panellists. The results are shown in FIG. 1. It clearly shows that the use of the invention product allows the improvement of both the intensity and the timing of the flavour release peak compared to use of conventional spray dried flavouring compositions using the same amount of flavouring in all the cases. In addition to this, it was shown that compared with the controlled release particles according to WO 91/17821, significantly higher flavour strength was experienced when the particulate composition according to the present invention was used.

Example 2

The particulate flavouring composition 2, described in Table 2 of Example 1 was coated with methyl cellulose by means of fluid bed coating, using an aqueous solution of 4 wt. % methyl cellulose. The coated product so obtained contained about 3 wt. % of methyl cellulose.

The coated product as well as the particulate flavouring composition 2 of Example 1 were added to the chewing gum base described in Example 1 in an amount of 1.5 wt. %. The release characteristics of the chewing gum products so obtained were evaluated by a sensorial panel in the same way as described in Example 1. The results of the evaluation are depicted in FIG. 2. These results clearly show that application of the methyl cellulose coating layer delays flavour release without affecting the release profile.

The invention claimed is:

1. A particulate composition comprising controlled release particles wherein discrete elements of flavouring-containing fat are dispersed in a gelatine matrix, said particles containing:
- 0.1-40 wt % of flavouring;
- 10-70 wt %, of gelatine;
- 0.1-75 wt % of said fat, which is selected from triglycerides, sucrose polyesters of fatty acids and combinations thereof, the fat having a melting point of at least 35° C.;
- 0.1-10 wt % of film forming carbohydrate selected from the group consisting of gums, modified starches, cellulose derivatives and mixtures thereof; and
- 1-30 wt % of carbohydrate plugging material selected from the group consisting of mono-, di- and trisaccharides and mixtures thereof; and
- said particles having a volume weighted average diameter of 50-1500 µm.

2. Composition according to claim 1, wherein at least 90% of the flavouring is dissolved or dispersed homogeneously in the discrete fat elements.

3. Composition according to claim 1, wherein the carbohydrate plugging material is selected from the group of glucose, fructose, maltose, sucrose, raffinose, xylitol, sorbitol and mixtures thereof.

4. Composition according to claim 1, wherein the gelatine has a bloom value of 10-300.

5. Composition according to claim 1, wherein the fat has a melting point of at least 38° C.

6. Composition according to claim 1, wherein the flavouring is selected from the group consisting of menthol flavouring, mint flavouring, eucalyptus flavouring and mixtures thereof.

7. Composition according to claim 1, wherein the composition comprises at least 50 wt % of the controlled release particles.

8. Composition according to claim 1, wherein the flavouring and fat contained within the controlled release particles are present as discrete elements that are entrapped within a matrix containing the gelatine.

9. Composition according to claim 1, wherein the combination of flavouring, gelatine, fat, film forming carbohydrate and plugging material constitutes at least 70 wt % of the particulate composition.

10. Composition according to claim 1, wherein the controlled release particles are obtainable by extrusion or spray drying of a solution or dispersion comprising flavouring, gelatine, fat, film forming carbohydrate, plugging material and a solvent or by fluidized bed coating of core particles with said solution or dispersion.

11. Composition according to claim 1, wherein the controlled release particles comprise an outer coating layer containing at least 50 wt % of a hydrocolloid selected from the group consisting of polysaccahrides, zein, shellac, cellulose derivatives and combinations thereof.

12. Composition according to claim 1, wherein:

$$((\text{Bloom number}/150)+(\text{wt \% gelatine}/30))*(\text{wt \% fat}/10) \geq 1.$$

13. Composition according to claim 1, wherein:

$$((\text{Bloom number}/150)+(\text{wt \% gelatine}/30))*(\text{wt \% fat}/10) < 1.$$

14. Flavour delivery system, comprising 5-70 wt % of a composition according to claim 2 and 5-70 wt % of a composition consisting of a carbohydrate plugging material selected from the group consisting of glucose, fructose, maltose, sucrose, raffinose, xylitol, sorbitol and mixtures thereof.

15. Flavour delivery system, comprising 5-70 wt % of a composition according to claim 2 and 5-70 wt % of liquid flavour.

16. A process for imparting controlled flavour release characteristics to chewing gum or toothpaste which comprises incorporating a particulate composition according to claim 1 to chewing gum or toothpaste.

17. Chewing gum or toothpaste comprising 0.01-6 wt % of a particulate composition according to claim 1.

* * * * *